US006500609B1

(12) United States Patent
Ribeill et al.

(10) Patent No.: US 6,500,609 B1
(45) Date of Patent: Dec. 31, 2002

(54) METHOD AND APPARATUS FOR SYNTHESIZING CHARACTERIZING AND ASSAYING COMBINATORIAL LIBRARIES

(75) Inventors: Yves Ribeill, Raleigh, NC (US); Pierre Monnet, Carroboro, NC (US); Jaleh Azmi Abedi, Raleigh, NC (US); Henry David Smith, III, Cary, NC (US); Susan Marie McComb, Cary, NC (US)

(73) Assignee: Scynexis Chemistry & Automation, Inc., Durham, NC (US)

( * ) Notice: Subject to any disclaimer, the term of this patent is extended or adjusted under 35 U.S.C. 154(b) by 0 days.

(21) Appl. No.: 09/248,541

(22) Filed: Feb. 11, 1999

(51) Int. Cl.[7] .............................................. G01N 33/00
(52) U.S. Cl. ...................... 435/4; 435/6; 435/DIG. 2; 435/DIG. 44; 435/DIG. 45; 436/43; 436/161; 422/68.1; 364/516; 210/656
(58) Field of Search ........................... 435/4, 6, DIG. 2, 435/DIG. 44, DIG. 45; 436/43, 161; 422/68.1; 364/516; 210/656

(56) References Cited

U.S. PATENT DOCUMENTS

| | | | |
|---|---|---|---|
| 3,589,867 A | 6/1971 | Heinz et al. .............. 23/230 R |
| 3,680,967 A | 8/1972 | Engelhardt ................. 354/246 |
| 3,853,010 A | 12/1974 | Christen et al. .............. 73/423 |
| 4,798,095 A | 1/1989 | Itoh ........................ 73/863.01 |
| 4,835,707 A | 5/1989 | Amano et al. .............. 364/497 |
| 5,267,178 A | 11/1993 | Berner ....................... 364/498 |
| 5,273,715 A | 12/1993 | Bridgham et al. ............ 422/63 |
| 5,301,261 A | 4/1994 | Poole et al. .................. 395/82 |
| 5,324,483 A | * 6/1994 | Cody et al. ................. 422/131 |
| 5,434,971 A | 7/1995 | Lysakowski, Jr. ........... 395/200 |
| 5,463,564 A | 10/1995 | Agrafiotis et al. .......... 364/496 |
| 5,489,678 A | 2/1996 | Fodor et al. ................ 536/22.1 |
| 5,503,805 A | 4/1996 | Sugarman et al. .......... 422/131 |
| 5,525,464 A | 6/1996 | Drmanac et al. .............. 435/6 |
| 5,527,681 A | 6/1996 | Holmes ......................... 435/6 |
| 5,541,061 A | 7/1996 | Fodor et al. .................... 435/6 |
| 5,545,531 A | 8/1996 | Rava et al. ..................... 435/6 |
| 5,547,839 A | 8/1996 | Dower et al. .................... 435/6 |
| 5,552,270 A | 9/1996 | Khrapko et al. ................ 435/6 |
| 5,556,762 A | 9/1996 | Pinilla et al. |
| 5,574,656 A | 11/1996 | Agrafiotis et al. .......... 364/500 |
| 5,595,664 A | 1/1997 | Sanford et al. ............. 210/656 |
| 5,609,826 A | 3/1997 | Cargill et al. .................. 422/99 |
| 5,639,603 A | 6/1997 | Dower et al. .................... 435/6 |
| 5,641,634 A | 6/1997 | Mandecki ....................... 435/6 |
| 5,658,799 A | 8/1997 | Choperena et al. ........... 436/50 |
| 5,670,054 A | 9/1997 | Kibbey et al. .............. 210/656 |
| 5,679,773 A | 10/1997 | Holmes ....................... 530/334 |
| 5,684,711 A | 11/1997 | Agrafiotis et al. .......... 364/500 |
| 5,690,893 A | 11/1997 | Ozawa et al. ................. 422/67 |
| 5,693,292 A | 12/1997 | Choperena et al. ........... 422/67 |
| 5,708,153 A | 1/1998 | Dower et al. ................ 536/22.1 |
| 5,712,171 A | * 1/1998 | Zambias et al. ............. 436/518 |
| 5,736,412 A | 4/1998 | Zambias et al. ............. 436/518 |
| 5,741,462 A | 4/1998 | Nova et al. .................. 422/68.1 |
| 5,757,659 A | 5/1998 | Arai et al. ................... 364/497 |
| 5,766,481 A | 6/1998 | Zambias et al. ............. 210/656 |
| 5,772,962 A | 6/1998 | Uchida et al. ................. 422/67 |
| 5,798,035 A | 8/1998 | Kirk et al. ................... 205/335 |
| 5,807,754 A | 9/1998 | Zambias et al. ............. 436/518 |
| 5,862,514 A | 1/1999 | Huse et al. .................... 702/22 |
| 5,874,214 A | 2/1999 | Nova et al. ..................... 435/6 |
| 5,901,069 A | 5/1999 | Agrafiotis et al. ........ 364/528.03 |
| 5,925,562 A | 7/1999 | Nova et al. ................. 435/287.1 |
| 5,938,932 A | 8/1999 | Connelly et al. ........... 210/659 |
| 5,942,387 A | 8/1999 | Hollinshead .................... 435/5 |
| 5,948,360 A | 9/1999 | Rao et al. ..................... 422/65 |
| 5,993,662 A | 11/1999 | Garr et al. .................. 210/656 |

FOREIGN PATENT DOCUMENTS

| | | |
|---|---|---|
| DE | 196 05 814 | 8/1997 |
| EP | 0882500 | 12/1998 |
| EP | 0 903 176 | 3/1999 |
| FR | 2 760 843 | 9/1998 |
| WO | 95 01559 | 1/1995 |
| WO | 96 05488 | 2/1996 |
| WO | 97/09353 | 3/1997 |
| WO | 97/10898 | 3/1997 |
| WO | 97/45443 | 12/1997 |
| WO | 98/15825 | 4/1998 |
| WO | 98/22219 | 5/1998 |

OTHER PUBLICATIONS

Weller et al., High Throughput Analysis . . . , Molecular Diversity, 1997, vol. 3, No. 1, 61–70.*

Schultz et al., High Throughput Purification . . . , Bioorganic and Medicinal Chemistry Letters, Sep. 1998 vol. 8, 2409–2414.*

Techniques and Experiments for Organic Chemistry, 2nd Edition, 1977.*

Bishop, C.A., et al., "High Performance Liquid Chromatography of Amino Acids, Peptides and Proteins XXI. The application of preparative reversed–phase high–performance liquid chromatography for the purification of a synthetic underivatised peptide," *Journal of Chromatography*, 192: 222–227, 1980.

(List continued on next page.)

*Primary Examiner*—Bennett Celsa
(74) *Attorney, Agent, or Firm*—Burns Doane Swecker & Mathis LLP

(57) ABSTRACT

Devices and processes for synthesizing, purifying and analyzing large numbers of compounds for use in combinatorial libraries, are disclosed. The processes involve generating a series of compounds in multi-well plates or multi-tube racks, purifying the reaction mixtures, analyzing the purified compounds, and optionally performing bioassays on the compounds. The information regarding the compounds is stored in a central database. The devices include one or more multi-tube arrays, a purification device, means for transferring the contents of the tubes, a solvent evaporator, analytical instrumentation, and, optionally, a weighing instrument. The multi-tube array(s) optionally include a cover, which can be placed on or removed from the array by computer control. By correlating the orientation of tubes from one stage to the next, it is possible to use a single bar code or other identifying mark for each multi-tube array rather than for each individual tube. This simplifies data collection for large numbers of compounds.

10 Claims, No Drawings

OTHER PUBLICATIONS

Bishop, C.A., et al., "The Preparative Separation of Synthetic Peptides on Reversed–Phase Silica Packed in Radially Compressed Flexible–Walled Columns," *J. Liquid Chromatography*, 4(4): 661–680, 1981.

Kaliszan, R., et al., "Quantitative Structure–Chromatographic Retention Relationships", *Chemical Analysis*, 91: 234–278 (Chapter 11), Wiley and Sons, New York, 1987.

Knighton, D.R., et al., "Facile, Semi–Preparative, High–Performance Liquid Chromatographic Separation of Synthetic Peptides Using Ammonium Bicarbonate Buffers," *Journal of Chromatography*, 249: 193–198, 1982.

Mirrlees, M.S., et al., "Direct Measurement of Octanol–Water Partition Coefficients by High–Pressure Liquid Chromatography," *J. Med. Chem.*, 19(5): 615–619, 1976.

DeWitt, S. H., et al., "Combinatorial Organic Synthesis Using Parke–Davis's DIVERSOMER Method", *Acc. Chem. Res.*, 29(3): 114–122, 1996.

Griffey, R. H., et al., "Rapid Deconvolution of combinatorial Libraries using HPLC Fractionation", *Tetrahedron, NL, Elsevier Sci. Pub.*, 54(16): 4067–4076, 1998.

Josses, P, et al., "Carrying out Multiple Reactions in Organic Synthesis with a Robot", *Advances in Laboratory Automation Robotics*, 5: 463–475, 1990.

Kibbey, C. E., "An Automated System for the Purification of Combinatorial libraries by Preparative LC/MS", *Laboratory Robotics and Automation*, 9: 309–321, 1997.

Lindsey, J. S., "A retrospective on the automation of laboratory synthetic chemistry", *Laboratory Automation & Information Management*, 17(1): 15–45, 1992.

Rudge, D. A., "The automation of solution phase synthetic chemistry using XP Zymate™ laboratory robotic systems", *Laboratory Automation & Information Management*, 33(2): 81–86, 1997.

Schultz, L., et al., "High Throughput Purification of Combinatorial Libraries", *Bioorganic & Medicinal Chemistry Letters*, 8(17): 2409–2414, 1998.

Garr, C. D., et al., "Solution Phase Synthesis of Chemical Libraries for Lead Discover", *J. Biomolec. Screening*, (Cephalon, Inc., West Chester, PA) 1(4): 179–186, 1996.

Testa et al., *Med. Res. Rev.* 11, pp. 35–48 (1991).

Harris et al, *High Throughput Analysis & Purification: The New Paradigm*, MDS Panlabs, Bothell, WA, pp. 1–13 (Mar. 1998).

Zeng, L., et al., "Automated analytical/preoperative high–performance liquid chromatography–mass spectrometry system for the rapid characterization and purification of compound libraries", *J. of Chrom. A*, (Elseiver science B.V.) 794: 3–13, 1998.

\* cited by examiner

METHOD AND APPARATUS FOR SYNTHESIZING CHARACTERIZING AND ASSAYING COMBINATORIAL LIBRARIES

FIELD OF THE INVENTION

This invention is generally in the area of the synthesis, purification, characterization and assay of combinatorial libraries of compounds.

BACKGROUND OF THE INVENTION

Before the advent of combinatorial chemistry, the development of new biologically active compounds was dependent on the rational design and synthesis of compounds with a structure similar to existing biologically active compounds. Scientists looked at structure-activity relationships (SARs) to rationally develop a small series of compounds which might be expected to have similar bioactivity. The types of compounds selected for testing typically belonged to narrowly defined chemical classes, such as peptides, steroids, and the like. Such a process is generally known as a rationl approach to synthesis.

The rational approach involved selecting a singular molecular candidate, prepared either via chemical synthesis or isolated from natural sources, and evaluating the molecular candidate for a particular bioactivity. (See, for example, Testa, B. & Kier, L. B. *Med. Res. Rev.* 1991, 11, 35–48 and Rotstein, S. H. & Murcko, M. A. *J. Med. Chem.* 1993, 36, 1700–1710.) The cycle was repeated until a molecule possessing the desirable properties was identified. The rational approach was necessary because the synthesis, purification, and evaluation of potential lead compounds was time consuming, labor intensive, and expensive.

One relatively new approach for identifying biologically active compounds is known as combinatorial chemistry. In this approach, libraries of compounds with structures similar to the existing biologically active compound are prepared in small quantities, but in large numbers, and the entire library can be evaluated, for example, using various binding studies.

Many useful drugs have been discovered through the screening of randomly chosen compounds rather than through the rational approach. Combinatorial libraries of randomly-built chemical structures are routinely screened for specific biological activity. (Brenner, S. & Lerner, R. A. *Proc. Natl. Acad. Sci. USA* 1992, 89, 5381). Rapid screening allows one to evaluate combinatorial libraries, as well as large numbers of compounds, related or not, whether or not they are produced through chemical synthesis or isolated from natural sources, or by using the rational approach.

Both solid phase and solution phase chemistry have been used to develop combinatorial libraries. Solid phase combinatorial chemistry has been used, for example, to prepare oligonucleotide and peptide libraries. A limitation of solid phase chemistry is the scale at which it can be performed. Solution phase chemistry is applicable to a wider variety of chemical reactions, and is more amenable to scaleup, other than solid phase chemistry.

A limitation with combinatorial chemistry is not only in generating new compounds, but purifying, analyzing and screening the compounds. Often, so many compounds can be synthesized that a bottleneck is created at the purification, chemical analysis, and bioassay stages.

Several methodologies have been developed to synthesize, purify, analyze and screen combinatorial libraries. Some of these involve preparing compounds in multi-well plates, and others involve multi-tube arrays. A limitation of using multi-well plates is that it the scale of the reactions tends to be rather limited due to the size of the wells, and it can be difficult to determine chemical yield, since it is difficult to obtain the weight of individual samples in a plurality of wells. Synthesizing compounds in multi-tube arrays allows one to scale up the synthesis somewhat, but suffers from the disadvantage that the tubes are not fixed in position, so that human error can occur if the tubes are misplaced.

Further, there is little standardization in the combinatorial chemistry field. For example, multi-tube arrays often include 48 or 96 tubes. However, automated purification and chemical analysis equipment is not necessarily designed around the number of tubes in the multi-tube arrays used to prepare the compounds. This makes it difficult to track the identity and properties of compounds as they progress through stages of synthesis, purification and chemical analysis.

Prior attempts at overcoming these limitations have typically involved placing individual labels eg., bar codes on each tube in a multi-tube array. The bar codes allow one to keep track of tubes which might have been misplaced due to human error, and also to keep track of tubes moved to and from different multi-tube racks with varying numbers of tubes per rack.

An example of a combinatorial approach that uses bar codes to track the synthesis, purification and chemical analysis of libraries of compounds is a system developed by MDS Panlabs. This system synthesizes compounds at a 1 mmole scale in multi-tube arrays, subjects the compounds to preparative scale HPLC, and analyzes the compounds by flow inject mass spectrometry. Each tube in the array is identified with a bar code, and is moved from stages of synthesis, purification and chemical analysis using robotic arms. The bar codes are typically attached using an adhesive, which can evaporate at any stage when the tubes are subject to conditions involving increased temperatures and/or reduced pressures.

Given the size of many combinatorial libraries, it may be a tremendous burden to place, and keep track of, individual bar-codes on a plurality of tubes. It would be advantageous to provide new devices and processes for analyzing and screening large numbers of compounds without the need to generate bar codes for each tube used to synthesize, characterize or otherwise handle the compounds. The present invention provides such devices and processes.

SUMMARY OF THE INVENTION

The present invention is directed to devices and processes for synthesizing, purifying and analyzing large numbers of compounds, in particular, those generated for use in combinatorial and lead optimization libraries.

The processes involve generating a series of compounds in multi-well plates or multi-tube racks, storing the location of the individual tubes in a computerized device, transferring the contents of each tube to a chromatographic device for purification/characterization, removing the solvent from each eluted fraction containing the compound of interest, chemically analyzing the compounds, and then optionally submitting them for bioassays, while maintaining the ability to correlate the position of the tubes in the original multi-well plate or multi-tube array to the position of the tubes generated or used in the next stage of the operation.

The devices include one or more multi-tube arrays, a chromatographic or other purification device, means for transferring the contents of the tubes to the purification device, a solvent evaporator, means for adding solvent to the solvent-evaporated tubes, analytical instrumentation, and a means for transferring some or all of the contents to, and optionally from, the analytical instrumentation. Optionally the devices include a weighing instrument.

In one embodiment, the multi-tube array(s) include a cover, which may be placed on or removed from the array by computer control. This permits the computer to move tubes from the multi-tube array to other locations, such as a weighing station, and also protects the tubes from being moved manually. This overcomes the need to place a bar code on each tube to minimize the types of human error which result in misplaced tubes, and minimizes the error associated with evaporation of adhesives on the bar code label, which can often be greater than ten percent of the weight of the sample.

In some embodiments, the number of tubes in the multi-tube arrays in each step is constant. Alternatively, the number of tubes can vary from one stage to the next. However, a correlation between the orientation of the tubes from one stage can be made with the orientation of the tubes in a subsequent stage.

By correlating the orientation of tubes from one stage to the next, it is possible to use a single bar code or other identifying mark for each multi-tube array rather than for each individual tube. This simplifies data collection for large numbers of compounds.

Compounds which can be evaluated using the process and methods described herein include, for example, pharmaceutical compounds and agricultural chemicals, such as insecticides, pesticides, and herbicides.

In one embodiment, the compounds are arranged in the multi-tube arrays in the form of arrays of different chemical compounds with a common structure, and are each modified in a controlled fashion to create a combinatorial library of structurally related compounds. The common structure preferably has one, and more preferably, at least two sites capable of undergoing a reaction to change the structure, usually by the addition of other molecules.

In one embodiment, the compounds are not synthesized using the devices and processes described herein, but are purified, analyzed and optionally subjected to bioassays after having been previously prepared.

The steps described above can be carried out globally on the array or individually on each tube. For example, during the synthesis step, reagents can be added globally to each of the tubes. During the purification step, the contents of the tubes can be individually transferred to a purification device. When the solvent is removed from the tubes, the entire rack can laced in a solvent removal device. When the reaction products are characterized, the contents of each tube can individually be sent to analytical instruments. Depending on the particular device which is used, those of skill in the art can readily optimize the process by performing certain steps globally and certain steps individually on the tubes in the arrays.

DETAILED DESCRIPTION OF THE INVENTION

The present invention is directed to devices and processes for synthesizing, purifying, and analyzing large numbers of compounds, in particular, those generated for combinatorial libraries and/or lead optimization libraries, using multi-well plates and/or multi-tube racks. As used herein, a combinatorial library is a library of compounds generated to find and/or generate lead compounds, and a lead optimization library is a library of compounds built around a previously identified lead compound. As used herein, substantially pure compounds are at least 40–60 percent pure, preferably 80 percent pure, and, more preferably, greater than 85 percent pure. As used herein, a tube is any suitable container that can contain from about 200 $\mu$g to about 1 g of a compound and preferably from about 1 mg to about 100 mg, of a compound throughout the processes defined herein.

The processes of the present invention involve:
a) synthesizing a series of compounds in multi-tube racks or multi-well plates,
b) storing the location of the individual tubes or wells in a computerized device,
c) individually transferring the contents of each tube or well to a device for purification,
d) removing the solvent from each purified fraction,
e) optionally weighing the individual tubes after the solvent has been removed to gain information regarding percent yield,
f) performing chemical analyses on the purified compounds, optionally
g) transferring the compound to one or more multi-well plates for subsequent bioassay; and
h) optionally performing bioassays on the purified compounds.

At each stage in the process, the position of the tube (or well, if the compounds are synthesized in a multi-well plate) in the previous stage can be correlated with the position of the tubes in the subsequent stage. This avoids the necessity to place a bar code on each individual tube. Rather, the process allows one to use a single code for each multi-tube array or multi-well plate, thus simplifying obtaining data for large numbers of compounds.

The devices include a multi-tube array, a chromatographic or other purification device, means for transferring the contents of the tubes to the purification device, a solvent evaporator, optionally a means for weighing the evaporated samples, a means for adding solvent to the solvent-evaporated tubes, analytical instrumentation, and a means for transferring some or all of the contents to, and optionally from, the analytical instrumentation.

The devices and processes described herein can be used for the rapid determination and optimization of desired biological or physical activity. An array can be screened and the optimum candidate chosen. This process can be continued in n dimensions to provide a structure activity relationship ("SAR") picture of the compounds of interest and the selection can be accelerated by the rapid modular synthesis of arrays for use in testing.

These arrays can be assembled to form a "super array" for exhaustive testing. In this embodiment, a large scale evaluation of a variety of different structures, functionalities and spatial arrangements can be carried out.

The apparatus and methods described herein can be used for the logical and rapid analysis of synthetic results for the assurance of purity and quality. One can determine the efficacy of a synthetic strategy by testing a series of loci within any given array. Accordingly, the general usefulness of various chemical reagents in a particular type of organic synthesis can be determined.

In addition to determining useful bioactive compounds, the devices and processes described herein can be used to facilitate the identification of optimal analyte or epitope binding ligands for attachment to a chromatographic support for separation or purification applications.

The devices and processes described herein provide for the complete control of the synthesis, purification, and/or analysis of entire libraries of compounds, without the need to identify each test-tube with a bar code. The lack of a bar code as an identifier allows for increased accuracy and decreased likelihood of error. This can be particularly relevant when the amount of the compound to be measured is on the same scale as the amount of adhesive lost to evaporation during the handling of the tubes.

Because the contents of each individual tube can be weighed, the amount of each compound which is prepared can be determined. This information can be useful in determining $LC_{50}$ data as well as in optimizing chemical syntheses.

By preparing a solution of the compounds and placing them into separate multi-well plates for subsequent bioassays, the tubes can be reused after cleaning without having to remove bar-codes. The tubes may be cleaned in bulk and re-weighed or it is also possible to clean the tubes individually and return them to their original position on the array such that the previously stored tared weight of the tube can be re-used, avoiding a re-measurement of the weight of the tubes.

I. Compound Synthesis

A. Types of Compounds Which Can be Synthesized

Any type of compound can be synthesized according to the processes described herein. In particular, libraries of pharmaceutical compounds and agricultural compounds can be synthesized. Typically, the compounds have a core structure which can be modified at at least one position, preferably two or more positions, with a variety of different functional groups, in order to generate a library, for example, a combinatorial or lead optimization library of compounds.

Typical core structures are linear, branched or cyclic organic compounds that include at least three carbon atoms and at least one, and preferably at least two sites capable of undergoing a reaction to change the structure, usually by the addition of other molecules to the reactive site.

Agricultural compounds which can be synthesized include insecticides, pesticides, herbicides, and the like. Examples of families of insecticides include 1-aryl pyrazoles, pyrroles, pyrrolidones, and nicotinic acid derivatives.

Pharmaceutical compounds which can be synthesized include, without limitation, steroids, hormones, peptides, proteins, oligonucleotides, oligoribonucleotides, enzymes, ligands which bind to various receptors, and the like.

Suitable core structures include, but are not limited to: peptides, proteins, oligonucleotides, oligoribonucleotides, oligosaccharides, alkaloids, quinolines, isoquinolines, benzimidazoles, benzothiazoles, purines, pyrimidines, thiazolidines, imidazopyrazinones, oxazolopyridines, pyrroles, pyrrolidines, imidazolidones, guinolones, amino acids, macrolides, penems, saccharides, xanthins, benzothiadiazine, anthracyclines, dibenzocycloheptadienes, inositols, porphyrins, corrins, and carboskeletons presenting geometric solids (e.g., dodecahedrane). The core structures can be derived from naturally occurring compounds, or can include non-natural modifications (i.e., non-naturally occurring amino acids and nucleotides).

Suitable modifications for the core structures include:

1) amino acid derivatives, which include, for example, natural and synthetic amino acid residues including all of the naturally occurring alpha amino acids, species having derivatives, variants or mimetics of the naturally occurring side chains; N-substituted glycine residues; natural and synthetic species known to functionally mimic amino acid residues, such as statin, bestatin, etc.

2) nucleotide derivatives, which includes natural and synthetic nucleotides, such as adenosine, thymine, guanidine, uridine, cytosine, derivatives of these and variants and mimetics of the purine ring, the sugar ring, the phosphate linkage and combinations of some or all of these. Nucleotide probes (between 2 and 25 nucleotides) and oligonucleotides (more than 25 nucleotides) including all of the various possible structural modifications; homo and hetero-synthetic combinations and permutations of the naturally occurring nucleotides; derivatives and variants containing synthetic purine or pyrimidine species, or mimics of these; various sugar ring mimetics; and a wide variety of alternate backbone analogs, including but not limited to phosphodiester, phosphorothionate, phosphorodithionate, phosphoramidate, alkyl phosphotriester, sulfamate, 3'-thioformacetal, methylene(methylimino), 3-N-carbamate, morpholino carbamate and peptide nucleic acid analogs.

3) a carbohydrate derivative, which would include natural physiologically active carbohydrates; related compounds, such as glucose, galactose, sialic acids, beta -D-glucosylamine and nojorimycin, which are both inhibitors of glucosidase; pseudo sugars, such as 5a-carba-2-D-galactopyranose, which is known to inhibit the growth of Klebsiella pneumonia (n=1); synthetic carbohydrate residues and derivatives of these (n=1) and all of the complex oligomeric permutations of these as found in nature, including high mannose oligosaccharides, the known antibiotic streptomycin (n>1).

4) a naturally occurring or synthetic organic structural motif. The term "motif" is defined as an organic molecule having or containing a specific structure that has biological activity, such as a molecule having a complementary structure to an enzyme active site, for example. This term includes any of the well known basic structures of pharmaceutical compounds including pharmacophores, or metabolites thereof. These basic structures include beta-lactams, such as penicillin, known to inhibit bacterial cell wall biosynthesis; dibenzazepines, known to bind to CNS receptors and used as antidepressants; polyketide macrolides, known to bind to bacterial ribosymes, etc. These structural motifs are generally known to have specific desirable binding properties to ligand acceptors.

5) a reporter element, such as a natural or synthetic dye or a residue capable of photographic amplification which possesses reactive groups that may be synthetically incorporated into the sulfaminimide structure or reaction scheme, and may be attached through the groups without adversely interfering or affecting with the reporting functionality of the group. Preferred reactive groups are amino, thio, hydroxy, carboxylic acid, carboxylic acid ester, particularly methyl ester, acid chloride, isocyanate alkyl halides, aryl halides and oxirane groups.

6) an organic moiety containing a polymerizable group such as a double bond, or other functionalities capable of undergoing condensation polymerization or copolymerization. Suitable groups include vinyl groups, oxirane groups, carboxylic acids, acid chlorides, esters, amides, azlactones, lactones and lactams. Other organic moiety such as those defined for R and R' may also be used.

7) a macromolecular component, such as a macromolecular surface or structures which may be attached to the sulfaminimide modules via the various reactive groups outlined above, in a manner where the binding of the attached species to a ligand-receptor molecule is not adversely affected and the interactive activity of the attached functionality is determined or limited by the macromolecule. Examples of macromolecular components include porous and non-porous inorganic components, such as, for example, silica, alumina, zirconia, titania and the like, as commonly used for various applications, such as normal and reverse phase chromatographic separations, water purification, pigments for paints, etc.; porous and non-porous organic macromolecular components, including synthetic components such as styrenedivinyl benzene beads, various methacrylate beads, PVA beads, and the like, commonly used for protein purification, water softening; and a variety of other applications, natural components such as native and functionalized celluloses, such as, for example, agarose and chitin, sheet and hollow fiber membranes made from nylon, polyether sulfone or any of the materials mentioned above. The molecular weight of these macromolecules may range from about 1000 Daltons to as high as possible. They may take the form of nano-particles (dp=1000–5000 Angstroms), latex particles (dp=1000–5000 Angstroms), porous or non-porous beads (dp=0.5–1000 microns), membranes, gels, macroscopic surfaces or functionalized or coated versions or composites.

Suitable chemical modifications also include chemical bonds to a suitable organic moiety, a radioactive moiety, a hydrogen atom, an organic moiety which contains a suitable electrophilic group, such as an aldehyde, ester, alkyl halide, ketone, nitrile, epoxide or the like; a suitable nucleophilic group, such as a hydroxyl, amino, carboxylate, amide, carbanion, urea or the like; or one of the other structural diversity elements defined below. In addition, the chemical modifications can be in the form of a ring, bi-cyclic or tri-cyclic ring system; or structure which connects to the ends of the repeating unit of the compound defined by the preceding formula; or may be separately connected to other moieties.

The modifications can be the same or different and each may be one or more atoms of carbon, nitrogen, sulfur, oxygen, any other inorganic elements or combinations thereof. For example, the core structure can be modified with cyano, nitro, halogen, oxygen, hydroxy, alkoxy, thio, straight or branched chain alkyl, carbocyclic aryl and substituted or heterocyclic derivatives thereof. The modifications can be in different in adjacent molecular cores and have a selected stereochemical arrangement about the carbon atom to which they are attached.

B. Types of Reactions Which Can be Performed

Virtually any type of reaction commonly performed in conventional combinatorial chemistry processes can be performed using the devices and processes described herein. The scale of the synthetic reactions is preferably in the range of greater than about 200 $\mu$g, more preferably between one and 100 mg, although the scale can be modified depending on the amount of compound necessary for the particular application.

The chemistry can be performed using solid phase or solution phase chemistry. Solution phase chemistry is advantageous because it is typically more amenable to scaleup than solid phase chemistry. Further, a wider variety of reactions and reaction conditions can typically be used with solution phase chemistry. Nevertheless, solid phase chemistry can be used to synthesize the compounds of interest.

Examples of reactions which can be done in either solid or solution phase include, for example, condensation reactions for preparing amides, esters, ureas, imines, and phosphorous compounds. Various carbon-carbon bond forming reactions can be performed using solid and solution phase chemistry. Examples include Suzuki reactions, organozinc reactions, Stille coupling reactions, Heck reactions, enolate alkylations, Wittig reactions, Homer-Wadsworth-Emmons reactions, metathesis reactions, such as ruthenium-catalyzed metathesis of polymer-bound olefins, Mitsunobu reactions, nucleophilic displacement of support-bound a-bromoamides in the submonomer preparation of peptoids, thiol alkylation, anilide alkylation with primary alkyl halides, one pot cyclization and anilide alkylation in the solid-phase synthesis of 1,4-benzodiazepine-2,5-diones, successive amide alkylations (generating new combinatorial peptide libraries from existing combinatorial peptide libraries), benzophenone imine α-carbon alkylation, alkylation or sulfonylation of a support-bound phenol, enolate monoalkylation, alkylation of support-bound 1,3-diketones in the solid-phase synthesis of pyrazoles and isoxazoles, tosyl displacement with primary or secondary amines, grignard reactions, SNAr reactions, Michael additions, iodoetherification reactions, oxidations, reductions, such as reductive alkylation, Pictet-Spengler reactions, and the like.

The types of reactions used to generate particular libraries will be expected to vary according to the types of compounds in the libraries as well as the types of substitutions which will be made. Those of skill in the art can readily determine appropriate sets of reactions and reaction conditions to generate the libraries of interest.

C. Organization of Compound Modifications in Multi-Tube Arrays

The compounds can be laid out in a logical fashion in multi-tube arrays or multi-well plates, in the form of arrays of chemical compounds. Preferably, the compounds all have a central core structure, and have various modifications which permit the identification of structure-activity relationships with which to determine optimum compounds for a particular use.

The physical, chemical and biochemical properties of the compound can be measured and correlated to specific chemical modifications of the core structure. The array can be ordered in such a fashion as to expedite synthesis, purification, and evaluation, to maximize the informational content obtained from the testing and to facilitate the rapid evaluation of that data.

The arrays can be constructed from logically ordered and arranged sub-arrays of compounds. Sub-arrays can be prepared which include spatially addressable sets of structurally related individual chemical compounds, with a common structure and a variable modification of the structure. Sub-arrays are particular useful when multiple positions on the structure are modified, and the variation between any two compounds within a given sub-array can include, for example, zero (0) or one (1) change in a structure.

These sub-arrays and arrays can be organized to form higher order arrays that include sets of arrays, and can be evaluated as a higher order array to provide information regarding the optimum structural features for the common core structure of interest.

The sub-arrays can be arranged in such a manner that the direct comparisons of compounds automatically yields information regarding the effect known fragments have on a desired application, as well as on the effect on changes in physical and reactive properties. As provided by simple set theory for any number of independently variable structural diversity elements n, there exists n logical higher order array arrangements, such that relational information on the effect of variation of each of the n structural diversity elements can be obtained in a similar manner by comparison of testing data from the relative addresses in appropriately arranged sub-arrays.

By screening all possible synthetic variations of a core molecule, the selection of the optimal candidate is more a function of the data collection method than the "rational" basis for selecting the compound. The desired physical and chemical properties, i.e., binding affinity and bioactivity, can be rapidly optimized, and directly correlated with the structural changes within a particular array or sub-array.

Because the spatial address of each compound within a multi-tube rack is known, the arrays can be tested to generate complete relational structural information such that a positive result provides: (1) information on a compound within any given spatial address; (2) simultaneous juxtaposition of this information upon a set of systematically structural congeners; (3) the ability to extract relational structural information from negative results in the presence of positive results.

D. Performing the Reactions

To perform the chemical reactions needed to synthesize a library of compounds, a compound with one or more reactive sites for carrying out chemical reactions is placed in a number of tubes. Appropriate reagents for carrying out the desired chemistry are added to the tubes, and the reactions allowed to take place. Robotic arms and multi-pipet devices can be used to add the appropriate reagents to the appropriate tubes. When appropriate, the chemistry can be performed in an inert atmosphere. The tubes can each be covered with a rubber septum to avoid contamination, and the reagents added via injection.

Preferably, the synthesis is carried out via computer control, where the location of each tube in a multi-tube array or each well in a multi-well plate is stored in a computer, and the identity of the compound to be synthesized is stored in the computer in a "memory map" or other means for correlating the data for the compound to the position of the tube or well.

Alternatively, the chemistry can be performed manually, preferably in multi-tube racks or multi-well plates, and the information stored on a computer. The compounds in the tubes can be purified, chemically analyzed, and optionally submitted for bioassays, in subsequent stages.

Preferably, the number of tubes in the multi-tube array or the number of wells in the multi-well plate in the synthesis stage is the same as the number of tubes in the multi-tube rack used in the purification stage and all subsequent stages, including chemical analysis and optionally bioassay. However, in one embodiment, the number of tubes in each stage can be different, as long as a correlation between the orientation of the tubes from one stage is made with the orientation of the tubes in each subsequent stage. This correlation is typically performed using relational database software, where various information regarding the contents of each tube is stored in a database.

II. The Device

A. Multi-well Plate or Multi-Tube Array

Any type of multi-well plate or multi-tube array commonly used in combinatorial chemistry can be used. Preferably, the number of wells or tubes is in excess of 30, and there is a tube in at least 60 percent of the positions in each multi-tube array. The shape of the rack is not important, but preferably, the rack is square or rectangular.

The tubes can be made, for example, from plastic, polymers, glass or metal, such as stainless steel, depending on the type of chemical reactions which are to take place in the tubes. The tubes can optionally be covered, for example, with a septum, which permits reagents to be added via a syringe, and also minimizes loss of product should the tube be jostled or otherwise mishandled, short of actually breaking the tube.

In one embodiment, the multi-tube array(s) include a cover, which can be placed on or removed from the array by computer control. The cover preferably includes a plurality of holes or other spaces which correspond to the tubes in the array. The holes are preferably not large enough for the tubes to be accidentally removed, but are large enough to allow for sample removal and solvent addition. In this manner, the computer can control the addition and removal of reagents from the tubes.

The application or removal of the cover may be achieved, for example, by inserting and removing a screw locking the cover in place, or using other locking mechanisms. This permits the computer to move tubes from the multi-tube array to other locations, such as a weighing station, and also protects the tubes from being moved manually. This overcomes the need to place a bar code on each tube to minimize the types of human error which result in misplaced tubes.

When a cover is placed over the array and septums are placed over each tube, it is possible to control the addition and removal of reagents from the tubes, as well as the removal of tubes from the array, using a computer. The possibility of human error is significantly minimized.

B. Means for Transferring the Contents of the Tubes

Any type of robotic arm which can transfer the tubes and the contents of the tubes to from one stage to the next, for example, from the purification device to the analytical device, can be used. Suitable robotic arms and robotic devices are well known to those of skill in the art of combinatorial chemistry, and include those by Zymart, Gilson, Hamilton, Bodhan and Tecan. The preferred robot is the Gilson 215 robot. The use of robotic arms to move tubes in combinatorial chemistry is known to those of skill in the art.

C. Purification Devices

Any device which can take the samples from the individual tubes and purify the resulting compounds can be used. Preferably, the device is a chromatographic device, such as a preparative scale HPLC, GC or column chromatography, although other devices can be envisioned, depending on the chemistry performed.

Preferably, in those embodiments in which a chromatographic column (HPLC, GC or column chromatography) is used, the device has the ability to identify when the compound of interest is eluting from the column. Various means have commonly been used to identify when compounds of interest are eluting from a column, including UV, IR, TLC, GC-MS, FID, NMR, ELSD, nitrogen detection and the like. Any of these means, and others known to those of skill in the art, can be used, alone or in combination.

When UV-active compounds are being prepared, the entire eluent from a chromatographic column is sent through a UV detector and then to a mass spectrometer. Sample collection can begin when the UV or mass spectrometry signal indicates the presence of the eluting compound, and can end when the UV signal indicates that the compound has finished eluting from the column. Mass spectrometry can verify that the eluted compound is really the compound of interest.

In one embodiment, the position of the tube prior to purification can be correlated to multiple tubes following purification, which permits the analysis of various different reaction products from a single reaction. Accordingly, the database can store information related to the reaction conditions used, the weight of each of the products obtained, the chemical analysis of each of the products, and, optionally, the bioactivity of the products as well.

If a chromatographic support is equipped with molecules which bind specifically with a component of the reaction mixture, that component will be separated from the mixture and can be released subsequently by changing the experimental conditions (e.g., buffers, stringency, etc.) This type of separation is known as "affinity chromatography" and is an effective and widely used separation technique. Accordingly, when it is possible to design appropriate conditions for performing affinity chromatography, it is preferred that affinity chromatography is used to separate the compounds.

Automatic sample collection is used to collect eluent fractions which include the compound of interest. Using the robotic arm, those fractions containing the compound of interest can be transferred to a second multi-tube array, wherein there is a correlation between the position of the tube in the original multi-tube array and the tube in the second multi-tube array.

Purification devices are used to automatically rinse the column of all impurities following elution of the compound of interest. Those of skill in the art can readily determine means for cleaning a purification device between runs. Further, it is also routine in the art for such devices to re-establish the appropriate solvent system for purifying the next type of compound being purified.

It is preferred that the purification device have the ability to perform automatic sample collection, rinse the column of impurities after the compound of interest has eluted, and re-establish solvent equilibrium before the next sample is purified.

Preferably, two or more purification devices can be run in series or parallel, such that while one column is being cleaned, the other column or columns can be purifying a reaction mixture. The use of multiple purification devices advantageously speeds up the purification stage.

One commercially available high throughput purification apparatus is the Biotage Parallex High Throughput Purification Station. This apparatus includes four preparative scale HPLC columns which are run in parallel. There are four pumps and a single injector which is valved to four sample loops. The pumps can be run, for example, with gradient solvent mixtures, for a first time period, a wash cycle for a second time period, and a solvent equilibration cycle for a third time period. The Biotage system includes an intelligent fraction collector which is triggered by signal to noise slope and threshold. The apparatus allows for collection of more than one compound from each tube following chromatographic separation.

D. Solvent Removal Apparatus

The multi-tube array containing the eluted fractions containing the various compounds of interest can be subjected to simultaneous solvent removal by subjecting the entire multi-tube array(s) to conditions which remove the solvent. In a preferred embodiment, the solvent is removed using a centrifuge which has the ability to receive a plurality of multi-tube racks.

Additional means for removing solvent from the tubes include placing the multi-tube rack(s) in a vacuum oven, or placing a device with a plurality of blowers designed to fit over the individual tubes, and blowing an inert gas over the contents of the tubes until the solvent is substantially removed, or can involve other means known to those of skill in the art for removing solvent.

E. Means for Weighing the Fractions

In some embodiments, it is desirable to weigh the individual tubes to determine the amount of material obtained in each synthesis. This can be readily accomplished by transferring the (preferably pre-weighed) tubes to a balance, and then back to the original place in the multi-tube rack. The information can be stored, for example, in a computer database. Any balance accurate enough for the scale at which the compound is present can be used. Preferably, a balance is used which is compatible with the robotic arms used to move the tubes from each stage to the next.

F. Means for Re-dissolving the Eluted Fractions

A robotic arm or other suitable means can be used to add an appropriate solvent to the solvent-evaporated tubes to re-dissolve the evaporated fractions in a solvent suitable for subsequent chemical analyses. In one embodiment, the means includes multi-pipet containing arms, each of which is capable of distributing an appropriate amount of solvent to each tube in the multi-tube rack.

The selection of solvent is dependent, in part, on the type of analyses to be performed on the compounds of interest. For example, if the compounds are to be analyzed by NMR, for example, $^1$H NMR or $^{13}$C NMR, then a deuterated solvent can be used. Some NMR instruments have the ability to substract solvent peaks, and the use of deuterated solvents is not a requirement with these instruments. However, this is not a requirement if the compounds are only to be subjected to GC-MS, IR, UV or other analyses. Those of skill in the art can readily determine an appropriate solvent or solvent system for use in a particular chemical analysis.

Preferably, the compounds of interest are dissolved in a deuterated solvent, and a fraction containing approximately 1 mg or less is analyzed by $^1$H NMR. When extremely powerful NMR instruments are used, even less sample can be evaluated. Optionally, following NMR analysis, the sample can be removed from the NMR tube or flow cell and returned to the original tube, thereby minimizing product loss.

Preferably, the NMR has the ability to transfer solutions of the compounds of interest to an NMR tube, run the NMR, transfer to the solution of a compound out of the NMR tube, clean out the tube automatically, and transfer a solution of the next compound to be evaluated to the NMR tube. This capability is present in at least one commercially available NMR instruments from Varian®.

Preferably, the compounds are analyzed by NMR, GC-MS, LC, ELSD and UV. Following chemical analysis, the racks of compounds can be transferred to a storage facility until bioassays are performed. In one embodiment, the chemicals are stored at a sufficiently cold temperature, for example, −15 to −20° C., that the compounds do not degrade significantly prior to the bioassay.

G. Bioassays

Following the chemical analyses, it can be desirable to evaluate the bioactivity of the compounds of interest. Methodology exists for performing multi-tube rack bioassays. Accordingly, the compounds of interest, in the multi-tube racks identified, for example, with a single bar code for the plate, can be sent off for bioassay and each tube in the rack identified by its position on the plate. This information can be stored electronically, for example, in a computer system.

Bioassays useful for a particular class of compounds are either well known or can be readily developed depending on the particular intended use of the compounds. When compounds are developed for binding to various receptors, numerous binding studies have been developed and described in the literature, which can readily be adapted to a combinatorial approach.

H. Computer System and Related Software

The device includes a computer system capable of storing the relative positions of the tubes in the multi-tube racks or wells in multi-well plates, as well as the data obtained for each tube. Software for managing the data is stored on the computer.

Relational database software can be used to correlate the position of the tubes at each stage of the process with the identify of the individual compounds, the analytical data from each compound, the percent yield of the chemical reactions used to obtain the compounds, and the optional bioassay data for each compound. Numerous commercially available relational database software programs are available, for example, from Oracle, Tripos, MDL, Oxford Molecular ("Chemical Design"), IDBS ("Activity Base"), and other software vendors.

Relational database software is a preferred type of software for managing the data obtained during the processes described herein. However, any software that is able to create a "memory map" of the positions of the tubes at each stage of the process and correlate that information with the information obtained at the other various stages can be used. This type of software is well known to those of skill in the art.

III. Methods of Identification and Analysis

Although the multi-tube rack need not contain compounds with similar core structures, it is preferred that they do so. In a preferred embodiment, the compounds were prepared using the chemistry described above.

The multi-tube racks or multi-well plates including a plurality of different compounds, located in individual tubes or wells, is subject to purification and analysis as described below.

A. Compound Purification

Using the computer software and hardware described above, the relative positions of the individual tubes, and therefore, the compounds within each tube, are stored in a database.

The robotic arms, with the means for transferring the contents of each tube, are used to individually, and in a stepwise manner, transfer the contents of the tubes, one by one, to the device used for purifying the compounds.

Following purification, the eluent fractions containing the compounds of interest are transferred from the purification device to the tubes in a second multi-tube array which correlates the position of the tubes in the second multi-tube array to the position of the tube or well in the first multi-tube array or multi-well plate. Preferably, the weight of each of the tubes in the second multi-tube array has been previously recorded in the database so that the weight of the compound, and, accordingly, the chemical yield, can be determined following removal of the solvent and subsequent weight of the solvent-evaporated tube.

Once the compounds in the tubes in the first multi-tube array have been purified and transferred to the second multi-tube array, the second multi-tube array can then be subjected to a solvent evaporation step.

Following solvent removal, the purified compounds, preferably with a purity exceeding about 80%, can then optionally be weighed, and then subjected to chemical analyses. The weight of the material and the results of the chemical analysis is preferably stored in the database.

B. Chemical Analyses

The contents of the tubes in the second multi-tube array, following solvent removal, can be re-dissolved in a suitable solvent, and subjected to chemical analyses by transferring the contents of the tubes to various devices for analysis, such as NMR, UV, IR, GC, GC-MS, and the like. The analytical data thus obtained can be stored by the computer and correlated to the compound of interest to which it pertains.

C. Bioassays

The compounds of interest, in the second multi-tube array, or in a third multi-tube array to which a portion of the compounds have been transferred, can be analyzed in bioassays to determine their bioactivity for a particular indication.

In one embodiment, the assays involve binding affinity studies, wherein the ability of the compounds to bind to a particular site are evaluated. Such studies are routine in the art, and typically do not involve a large amount of material. Using these studies, and correlating the results of the studies with the compounds using the same database used to identify and characterize the compounds, one can generate a large amount of bioactivity date in a relatively short amount of time using a relatively small amount of material.

Generally, bioassays involve in-vitro and in-vivo screening tests of the compounds so generated, eg., insecticidal, fungicidal, herbicidal, pharmaceutical, or veleunary tests.

The apparatus and methods described herein will be better understood with reference to the following non-limiting example.

Generic Synthesis, Purification, Analysis and Distribution Procedure

A library of 96 individual compounds is synthesized by chemical reactions in a 96-well plate, the wells of which are arranged in an abscissa and ordinate two dimensional configuration. The contents of each well is submitted individually to a preparative high pressure liquid chromatography (HPLC) system. 96 purified products (as detected by a mass spec detector) are collected into a series of tubes in racks each rack of which is labeled with a bar code for identity. The identity of the contents of each tube, its position in the rack and the rack's bar-code are recorded in a database on a computerized database. The racks are transferred to an analytical HPLC and the bar-codes read. An analytical HPLC trace is recorded using ultraviolet (UV) and electron light scattering detector (ELSD) detectors and this data recorded in the database. The racks are transferred to a centrifugal evaporator and the solvent removed from all the tubes at once. The racks are then transferred to a system equipped with a robotic arm, a bar-code reader and a balance so that the weight of each tube can be recorded. This information is transferred to the central server where the tare weight of each tube had already been recorded and thus the weight of material in each tube can be calculated. The racks are transferred to a liquid handler, the bar-code is read and the contents of the tubes are diluted to a predetermined concentration using the weight of material recorded on the central server. The rack is transferred to an NMR, the bar-code is read and the $^1$H NMR is recorded and stored on the central server. All of the analytical data is viewed and a decision regarding what biological testing is required is made and recorded on the central server. The racks are transferred to a distribution device, the bar-code is read and samples for testing are prepared based on the decisions recorded on the central server. Any excess material is transferred to a storage vessel. The tubes in the rack are replaced with fresh tubes and the rack recycled through the process.

In all transformations, the computer database tracks the movement of the compound so synthesized from the 96-well plate to the end of the process. The racks are the only devices that are bar-coded for identity.

We claim:

1. A process for synthesizing, purifying, and analyzing a plurality of compounds while tracking the compounds by position alone using a relational database comprising:
   a) synthesizing a series of reaction mixtures in a first multi-well plate or multi-tube array;
   b) storing information regarding each synthesis in the relational database according to the position of each reaction mixture in the first plate or array;
   c) transferring the reaction mixtures in the first wells or tubes to a liquid chromatography purification device selected from the group consisting of preparative scale HPLC and column chromatography;
   d) submitting the reaction mixtures to a purification process which produces one or more eluent fractions comprising individual compounds;
   e) transferring the eluent fraction(s) comprising individual compounds to one or more wells or tubes in a second multi-well plate or multi-tube array;
   f) correlating the compounds to the reaction mixtures using the position of the wells or tubes in the multi-well plates or multi-tube arrays using the relational database;
   g) analyzing the individual compounds in the wells or tubes of the second multi-well plate or multi-tube array;
   h) storing information regarding the analysis of the compounds in the relational database according to the position of each compound in the second multi-well plate or multi-tube array; and
   i) correlating the information regarding the analysis of each compound to the reaction mixtures using the position of the wells or tubes in the multi-well plates or multi-tube arrays using the relational database;
   wherein the wells or tubes are not individually labeled and the information regarding the compounds including the analysis of the compounds and the synthesis of the compounds is tracked and correlated by only the position of each tube or well in the various multi-well plates or multi-tube arrays.

2. The process of claim 1, wherein solvent is removed from the tubes following purification and transfer of the eluent fraction or fractions of the tubes in the second multi-tube array.

3. The process of claim 2, wherein the tubes in the second multi-tube array are weighed prior to receiving the eluent fraction and after the solvent has been removed.

4. The process of claim 3, wherein the weight of each purified compound is obtained by subtracting the weight of the empty tube from that of the solvent-evaporated tube in the second multi-tube array, and that information is stored in the database.

5. The process of claim 1, wherein the first and second multi-tube arrays are arranged in abcissa and ordinate configurations.

6. The process of claim 1, wherein the synthesized, purified and analyzed compounds are further subjected to one or more bioassays.

7. The process of claim 6, wherein results of the bioassay of the compounds are correlated with the stored information regarding the compounds using the position of the tubes in the multi-tube array using the relational database.

8. A method of automated chemical synthesis of a chemical library which comprises:
   a) disposing an array of tubes, each of which contains at least one core compound, on a rigid support, wherein each tube is in a fixed location in the array;
   b) storing information regarding the core compound in a relational database according to the location of each core compound on the rigid support;
   c) performing a chemical reaction on the core compounds to form an array of reaction mixtures containing an array of reaction products;
   d) storing information regarding the chemical reaction and the reaction mixtures in the relational database according to the location of each reaction mixture on the rigid support;
   e) purifying the reaction mixtures using preparative scale HPLC or column chromatography and isolating the reaction products,
   f) storing information regarding the reaction product in the relational database according to the location of each reaction product on the rigid support;
   g) characterizing the reaction products with one or more analytical instruments;
   h) storing information regarding the characterization of each reaction product in the relational database according to the location of each reaction product on the rigid support; and
   i) optionally repeating one or more of steps a–d,
   wherein the tubes are not individually labeled;
   at least one or more of the steps is effected globally on the array and at least one of the steps is effected on each tube individually; and
   the information stored in the relational database is tracked and correlated by only the location of each tube on the rigid support.

9. The method of claim 8 wherein the amount of isolated reaction product in each tube is calculated by obtaining a tare weight of the tubes, obtaining the weight of the previously tared tubes after the reaction products are isolated in the tubes and all solvent is removed, and subtracting the tare weight of the tubes from the weight of the tubes containing the reaction products.

10. A process for synthesizing, purifying, and analyzing a plurality of compounds while tracking the compounds by position alone using a relational database comprising:
   a) synthesizing a series of reaction mixtures in a first multi-well plate or multi-tube array comprising individual wells or tubes;
   b) purifying the reaction mixtures producing one or more eluent fractions comprising individual compounds; and
   c) analyzing the individual compounds;
   wherein the wells or tubes are not individually labeled and information regarding the compounds including the analysis and the synthesis is tracked and correlated by only the position of each tube or well in the multi-well plates or multi-tube arrays using the relational database.

* * * * *

UNITED STATES PATENT AND TRADEMARK OFFICE
CERTIFICATE OF CORRECTION

PATENT NO. : 6,500,609 B2
DATED : December 31, 2002
INVENTOR(S) : Yves Ribeill et al.

It is certified that error appears in the above-identified patent and that said Letters Patent is hereby corrected as shown below:

<u>Column 15,</u>
Line 43, after "fractions" delete "of" and insert therefor -- to --.

Signed and Sealed this

Twelfth Day of August, 2003

JAMES E. ROGAN
*Director of the United States Patent and Trademark Office*